(12) United States Patent
Zhou et al.

(10) Patent No.: US 9,567,214 B2
(45) Date of Patent: Feb. 14, 2017

(54) CHEMICAL SENSING DEVICE

(71) Applicant: Hewlett-Packard Development Company, L.P., Houston, TX (US)

(72) Inventors: Zhang-Lin Zhou, San Diego, CA (US); Zhiyong Li, Foster City, CA (US); Steven J. Barcelo, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/763,491

(22) PCT Filed: Jan. 25, 2013

(86) PCT No.: PCT/US2013/023266
§ 371 (c)(1),
(2) Date: Jul. 24, 2015

(87) PCT Pub. No.: WO2014/116238
PCT Pub. Date: Jul. 31, 2014

(65) Prior Publication Data
US 2015/0355097 A1    Dec. 10, 2015

(51) Int. Cl.
*B82Y 15/00* (2011.01)
*G01N 21/65* (2006.01)
*G01N 21/552* (2014.01)
*G01N 21/64* (2006.01)

(52) U.S. Cl.
CPC ............. *B82Y 15/00* (2013.01); *G01N 21/554* (2013.01); *G01N 21/648* (2013.01); *G01N 21/658* (2013.01); *G01N 2021/651* (2013.01)

(58) Field of Classification Search
CPC ..... B82Y 15/00; G01N 21/554; G01N 21/648; G01N 21/658; G01N 2021/651
See application file for complete search history.

(56) References Cited

U.S. PATENT DOCUMENTS

| | | |
|---|---|---|
| 7,163,659 B2 | 1/2007 | Stasiak et al. |
| 7,245,370 B2 | 7/2007 | Bratkovski et al. |
| 7,388,200 B2 | 6/2008 | Stewart et al. |
| 7,579,077 B2 | 8/2009 | Dubrow et al. |
| 7,911,010 B2 | 3/2011 | Stetter |

(Continued)

FOREIGN PATENT DOCUMENTS

| | | |
|---|---|---|
| CN | 102834709 | 12/2012 |
| EP | 1992938 A1 | 11/2008 |

(Continued)

OTHER PUBLICATIONS

Bendikov et al. (Anal. Chem., 2008, 80:7487-7498).*

(Continued)

*Primary Examiner* — Jeremy C Flinders
(74) *Attorney, Agent, or Firm* — HP Inc. Patent Department (57) ABSTRACT

The present disclosure is drawn to chemical sensing devices and associated methods. In one example, a chemical sensing device can include a substrate; an elongated nanostructure having an attachment end and a free end opposite the attachment end, the attachment end affixed to the substrate and the free end including a metal; and a metal oxide coating applied to the elongated nanostructure. In one example, a functional group can be attached to the coating via a covalent bond.

20 Claims, 5 Drawing Sheets

(56) References Cited

U.S. PATENT DOCUMENTS

| | | |
|---|---|---|
| 8,048,377 B1 | 11/2011 | Zhou et al. |
| 2005/0130163 A1 | 6/2005 | Smith et al. |
| 2006/0292839 A1 | 12/2006 | Yi et al. |
| 2008/0094621 A1 | 4/2008 | Li et al. |
| 2009/0137411 A1 | 5/2009 | Sun et al. |
| 2009/0233349 A1 | 9/2009 | Petersen et al. |
| 2010/0129623 A1 | 5/2010 | Johansson et al. |
| 2011/0150701 A1 | 6/2011 | Lee et al. |
| 2011/0166045 A1 | 7/2011 | Dhawan et al. |
| 2012/0058470 A1 | 3/2012 | Chelyapov et al. |
| 2012/0092660 A1 | 4/2012 | Wu |
| 2012/0130050 A1 | 5/2012 | Tada et al. |
| 2013/0040862 A1 | 2/2013 | Li et al. |

FOREIGN PATENT DOCUMENTS

| | | |
|---|---|---|
| JP | 2007530925 | 11/2007 |
| JP | 2010-230352 | 10/2010 |
| JP | 2011-033539 | 2/2011 |
| WO | WO-2005093419 | 10/2005 |
| WO | WO-2006/073117 | 7/2006 |
| WO | WO-2011114812 | 9/2011 |
| WO | WO-2012079018 | 6/2012 |

OTHER PUBLICATIONS

Formo, Eric V. et al. "Robust SERS substrates generated by coupling a bottom-up approach and atomic layer deposition." ACS Applied Materials & Interfaces 2, No. 7 (2010): 1987-1991.

John, Joshy F., et al. "Use of atomic layer deposition to improve the stability of silver substrates for in situ, high-temperature SERS measurements." Journal of Raman Spectroscopy 41, No. 1 (2010): 4-11.

European Search Report (Supplemental), Nov. 23, 2015, EP Patent Application No. 13872987.6, 5 pages.

Hu, Min, et al. "Gold nanofingers for molecule trapping and detection." Journal of the American Chemical Society 132, No. 37 (2010): 12820-12822.

Klutse, Charles K. et al. "Optimization of SAM-based multilayer SERS substrates for intracellular analyses: the effect of terminating functional groups." SPIE Defense, Security, and Sensing. International Society for Optics and Photonics, 2011.

International Search Report, KIPO, Oct. 11, 2013, PCT Patent Application No. PCT/US2013/023266.

"Nanostructure", In: Wikipedia, May 19, 2016, XP055273743.

* cited by examiner

CHEMICAL SENSING DEVICE

CROSS-REFERENCE TO RELATED APPLICATION

This application is a U.S. National Stage Application of and claims priority to International Patent Application No. PCT/US2013/023266, filed on Jan. 25, 2013, and entitled "CHEMICAL SENSING DEVICE," which is hereby incorporated by reference in its entirety.

BACKGROUND

Systems for performing molecular analysis can include the use of surface-enhanced Raman spectroscopy (SERS), enhanced fluorescence, enhanced luminescence, and plasmonic sensing, among others. With specific regard to SERS, Raman spectroscopy is a spectroscopic technique used in condensed matter physics and chemistry to study various low-frequency modes in molecular systems. In further detail, in a Raman spectroscopic, an approximately monochromatic beam of light of a particular wavelength range passes through a sample of molecules and a spectrum of scattered light is emitted. The spectrum of wavelengths emitted from the molecule is called a "Raman spectrum" and the emitted light is called "Raman scattered light." A Raman spectrum can reveal electronic, vibrational, and rotational energies levels of a molecule. Different molecules produce different Ra-man spectrums that can be used like a fingerprint to identify molecules and even determine the structure of molecules. With this and other sensing techniques, enhancing device sensitivity, simplifying sensors, providing additional flexibility, etc., in such devices would be desirable.

BRIEF DESCRIPTION OF THE DRAWINGS

Additional features and advantages of the disclosure will be apparent from the detailed description which follows, taken in conjunction with the accompanying drawings, which together illustrate, by way of example, features of the disclosure.

Reference will now be made to the exemplary embodiments illustrated, and specific language will be used herein to describe the same. It will nevertheless be understood that no limitation of the scope of the disclosure is thereby intended.

DETAILED DESCRIPTION

Raman spectroscopy can be used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy is a useful technique for a variety of chemical or bio-logical sensing applications. However, the intrinsic Raman scattering process is very inefficient, and rough metal surfaces, various types of nano-antennas, as well as waveguiding structures have been used to enhance the Raman scattering processes (i.e., the excitation and/or radiation process described above).

The Raman scattered light generated by a compound (or ion) adsorbed on or within a few nanometers of a structured metal surface can be over 100 times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

Most SERS systems only enhance the electro-magnetic field at certain hot spots. While this can be desirable, in many cases, the analytes are spread evenly on the SERS substrate, such as by simple adsorption. However, only a small fraction of the analytes actually populates the hot spots.

In accordance with this, it has been recognized that it would be advantageous to develop a chemical sensing device based on a new class of structures. These structures can be particularly useful for surface-enhanced Raman spectroscopy (SERS), but may also be useful with other sensing techniques. Specifically, the present devices can contain a plurality of elongated nanostructures affixed to a substrate with a free end having a metallic coating or cap, where the nanostructures are coated with a metal oxide coating. The present nanostructures can flex and trap molecules which can then be sensed using SERS techniques. Further, in some specific examples, the present nanostructures can include functional groups (e.g. ligands containing functional groups) attached to the metal oxide coating applied to the metallic coating or cap, thereby providing additional selectivity and sensitivity previously unachieved.

It is noted that when discussing a chemical sensing device, a method of stabilizing a nanostructure, or a method of making a chemical sensing device, each of these discussions can be considered applicable to the other embodiment, whether or not they are explicitly discussed in the context of that embodiment. Thus, for example, in discussing a functional group for a chemical sensing device, such a functional group can also be used in a method of making a chemical device, and vice versa.

Thus, a chemical sensing device can include a substrate; an elongated nanostructure having an attachment end and a free end opposite the attachment end, the attachment end affixed to the substrate and the free end including a metal; a metal oxide coating applied to the elongated nanostructure; and a functional group attached to the coating via a covalent bond.

As used herein, the term "nanostructure" refers to any structure having dimensions of width or diameter less than 1 micron. As such, an elongated nanostructure can include structures that have an aspect ratio with a length at least two times longer than the shortest width. Examples can include nanocones, nanopyramids, nanorods, nanobars, nanofingers, nanopoles and nanograss, without limitation thereto. As used herein, the terms "nanocones," "nanopyramids," "nanorods," "nanobars," "nanopoles" and "nanograss," refer to structures that are substantially: conical, pyramidal, rod-like, bar-like, pole-like and grass-like, respectively, which have nano-dimensions as small as a few tens of nanometers (nm) in height and a few nanometers in diameter, or width. For example, flexible columns may include nano-columns having the following dimensions: a diameter of 10 nm to 500 nm, a height of 20 nm to 2 micrometers (μm), and a gap between flexible columns of 20 nm to 500 nm. The terms of art, "substantially conical," "substantially pyramidal," "substantially rod-like," "substantially bar-like," "substantially pole-like" and "substantially grass-like," refers to structures that have nearly the respective shapes of cones, pyramids, rods, bars, poles and grass-like asperities within the limits of fabrication with nanotechnology.

As used herein, the term "metallic cap" refers to nanostructures, including nanospheres, prolate nanoellipsoids, oblate nanoellipsoids, nanodisks, and nanoplates, having a width or diameter of 500 nm or less. In one example, the metallic cap may possess shape-induced magnetic anisotropy. As used herein, the terms "nanospheres," "prolate nanoellipsoids," "oblate nanoellipsoids," "nanodisks," and "nanoplates," refer to structures that are substantially: spherical, prolate ellipsoidal, oblate ellipsoidal, disk-like, and plate-like, respectively, which have nano-dimensions as small as a few nanometers in size: height, diameter, or width. In addition, the terms "substantially spherical," "substantially prolate ellipsoidal," "substantially oblate ellipsoidal," "substantially disk-like," and "substantially and plate-like," refers to structures that have nearly the respective shapes of spheres, prolate ellipsoids, oblate ellipsoids, disks, and plates within the limits of fabrication with nanotechnology.

Generally, the elongated nanostructure can include a non-metallic column with a metallic coating or metallic cap. In one example, the nanostructure can include a polymer, such as a resist, coated with a SERS-active metal, such as gold, silver, copper, platinum, aluminum, etc. or the combination of those metals in the form of alloys. Generally, the SERS active metal can be selectively coated on the tips of the non-metallic column or deposited thereon. In addition, the SERS active metal can be a multilayer structure, for example, 10 to 100 nm silver layer with 1 to 50 nm gold over-coating, or vice versa. Additionally, the SERS active metal can be further coated with a thin dielectric layer.

Generally, the use of a polymer can render the nanostructures sufficiently flexible to permit the bending so that the tips meet at the top of the structure. Additionally, it is noted that the polymer used to form the nanostructure can be insulating, or can be conductive or semi-conductive. Examples of suitable polymers include, but are not limited to, polymethyl methacrylate (PMMA), polycarbonate, siloxane, polydimethylsiloxane (PDMS), photoresist, nanoimprint resist, and other thermoplastic polymers and UV curable materials including one or more monomers/oligomers/polymers. In another example, the nanostructures can include an inorganic material having sufficient flexibility to bend. Examples of such inorganic materials include silicon oxide, silicon, silicon nitride, alumina, diamond, diamond-like carbon, aluminum, copper, and the like.

Once the basic elongated nanostructures are formed on the substrate (by deposition, growth, or any other technique known in the art to apply nanostructures on a substrate), they can be coated with a metal oxide coating. It is noted that the metal oxide coating is an affirmatively applied coating, and is not merely an oxidized surface of the elongated nanostructure. In one example, the metal oxide can include silicon oxide, titanium oxide, zinc oxide, aluminum oxide, gallium oxide, indium oxide, zirconium oxide, hafnium oxide, tantalum oxide, and mixtures thereof. In one aspect, the metal oxide can be silicon oxide. The metal oxide coating can be done by various methods such as coating or depositing. Such methods can include atomic layer deposition (ALD) or E-beam sputtering method. In one example, the thickness of the coating can range from 1 nm to 200 nm. In another aspect, the coating can be from 2 to 50 nm.

Notably, such a coating can provide several benefits. First, the coating can extend the life of the chemical sensing device. In one example, the coating increases the shelf life of the nanostructure by 100% compared to a comparable nanostructure, the comparable nanostructure substantially identical to the nanostructure except not having the metal oxide coating. As discussed above, such increase in shell life can apply to the chemical sensing device. As used herein, "shelf life" refers to the operational life of the device or component. Second, the metal oxide coating can, in some instances, provide better selectivity than the uncoated metal surface. Third, the metal oxide coating can protect the underlying metal from oxidizing. Fourth, the metal oxide coating can provide a better surface for attachment of functional groups and ligands as described herein.

The chemical sensing device generally includes functional groups attached to the metallic coating or cap. In one example, the functional group can have a ligand-type structure including an attachment functional group (A), a spacer group (B), and a functional group (FG) according to formula I:

$$A\text{-}B\text{-}FG \qquad (I)$$

where A is an attachment functional group that attaches to the metal oxide coating on the nanostructure, B is substituted or unsubstituted, linear or branched alkyl or aryl, and FG is an target organic functional group capable of binding to a target molecule.

The attachment functional group can include any group that is capable of covalent bonding to the metal oxide coating, including hydroxyl groups on the surface of the oxide coating. Such attachment functional groups may include trichlorosilyl groups, trimethoxysilyl groups, triethoxysilyl groups, tripropoxysilyl groups, etc. Other attachment functional groups can include carboxylic acid chlorides, sulfonyl chlorides, isocyanates, and active carboxylic acid esters.

The spacer group generally includes any group of atoms that covalently bond the attachment functional group to the organic functional group. In one aspect, the spacer group can be a $-(CF_2)_n-$ where n ranges from 1 to 15.

The target organic functional group can include any moiety that is capable of interacting (including ionic, coordinate, or covalent bonding) with a target molecule. The target organic functional groups can include the functional groups as discussed herein, alone, or in combination with more complex structures, e.g., methyl red dye. In one example, the organic functional group can include acidic functional groups or their corresponding salt forms, including but not limited to, —OH, —SH, —COOH, —CSSH, —COSH, —SO$_3$H, —PO$_3$H, —OSO$_3$H, —OPO$_3$H, etc. In another example, the organic functional group can include basic functional groups or their corresponding salts, including but not limited to, trialkylamine R$_1$R$_2$N—, pyridines or substituted pyridines, imidazoles or substituted imidazoles; wherein R$_1$ and R$_2$ can be independently any alkyl or branched alkyl groups, which include, but not limited to, hydrogen, methyl, ethyl, propyl, isopropyl, butyl, iso-butyl, n-octyl, n-decyl, n-dodecyl, n-tetradecyl, etc.

The chemical sensing device generally includes a functional group formulated to selectively bind a target molecule. The target molecule can be a metal ion, an organic compound, or a hydrogen ion. In one example, the target molecule is a metal ion and the functional group is formulated to selectively bind the metal ion. In one example, the metal ion can include chromium, lead, mercury, zinc, calcium, sodium, hydrogen, potassium, arsonium, and mixtures thereof. Additionally, the target molecule can be an organic compound of interest. In one example, the organic compound can be melamine, pesticides, ractopamine, plasticizers, bisphenol A, potential explosives such as dinitrotoluenes, dinitrophenols, trinitrotoluenes, trinitrophenols, and mixtures thereof.

When separating from a liquid, the target molecules may be soluble in common solvents. Such common solvents can include methanol, ethanol, isopropanol, hexafluoro-isopropanol, toluene, chloroform, tetrahydrofuran, acetone, acetonitrile, xylenes, ethyl acetate, hexanes, dichloromethane, etc.

By using the present functional groups, the chemical sensing device can be sensitive enough to detect a target molecule; including a metal ion, an organic compound, or a hydrogen ion; at a concentration as low as 1 part-per-million (ppm). In one aspect, the sensitivity can be as low as 1 part-per-billion (ppb), and in one specific aspect, as low as 1 part-per-trillion (ppt).

Regarding sensitivity, the present chemical device can include a plurality of elongated nanostructures attached to a substrate forming an array. In one example, the array can include sub-arrays. In another aspect, the sub-arrays can each have individual selectivity for a target molecule. As such, one array can have selectivity for a plurality of target molecules. The chemical sensing device can be further configured to detect the target molecule from a liquid or gas.

Additionally, the chemical sensing device can further include a detector operatively coupled to the nanostructure. In one example, the detector can be a colorimeter, a reflectometer, a spectrometer, a spectrophotometer, a Raman spectrometer, an optical microscope, and/or an instrument for measuring luminescence.

Figure 1:
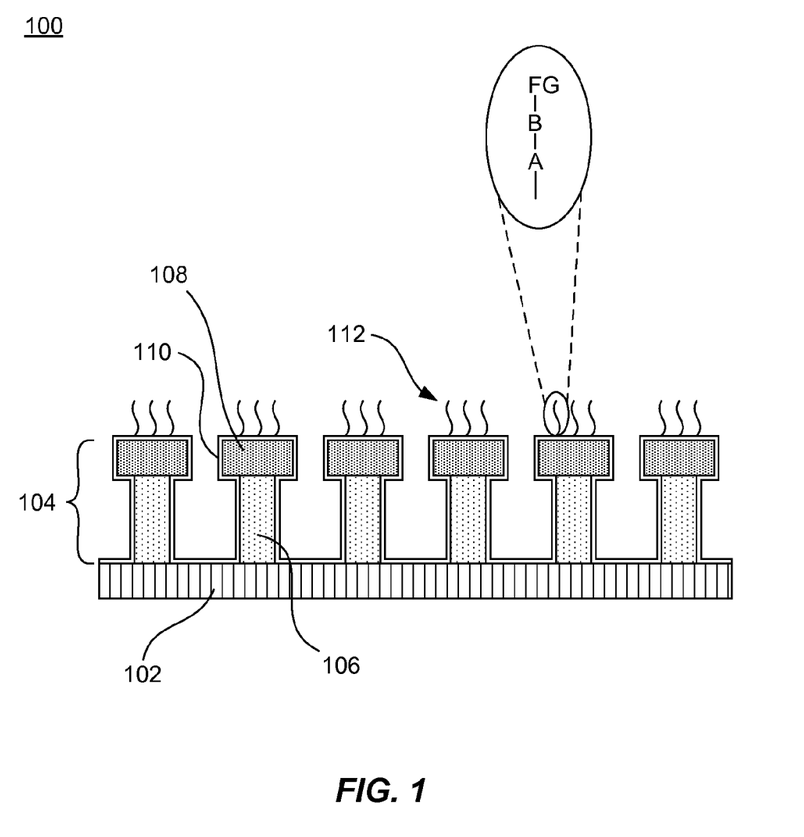
FIG. 1 is a cross-sectional view of a chemical sensing device in accordance with an example of the present disclosure.

Referring to FIG. 1, a chemical sensing device 100 can include a substrate 102 having an elongated nanostructure 104 attached thereto. The elongated nanostructure has a columnar structure 106 with a metallic cap 108 deposited thereon. Further, the elongated structure and substrate can be coated with a metal oxide coating 110 and can further include functional groups 112 covalently bonded to the metal oxide coating. As shown in the insert, in one example, the functional groups can generally includes a ligand-type structure A-B-FG, where A is an attachment functional group that binds the ligand to the metallic cap, B is a spacer group, and FG is a target organic functional group coupled to the attachment functional group through the spacer group. While the present figure provides a specific structure of the chemical sensing device, it is understood that the illustrated structure is not intended to be limiting and that the present disclosure contemplates the use of various elements as discussed herein. For example, the present target organic functional group could be bound directly to the metal oxide coating without the need for a spacer group and/or attachment functional group.

Figure 2:
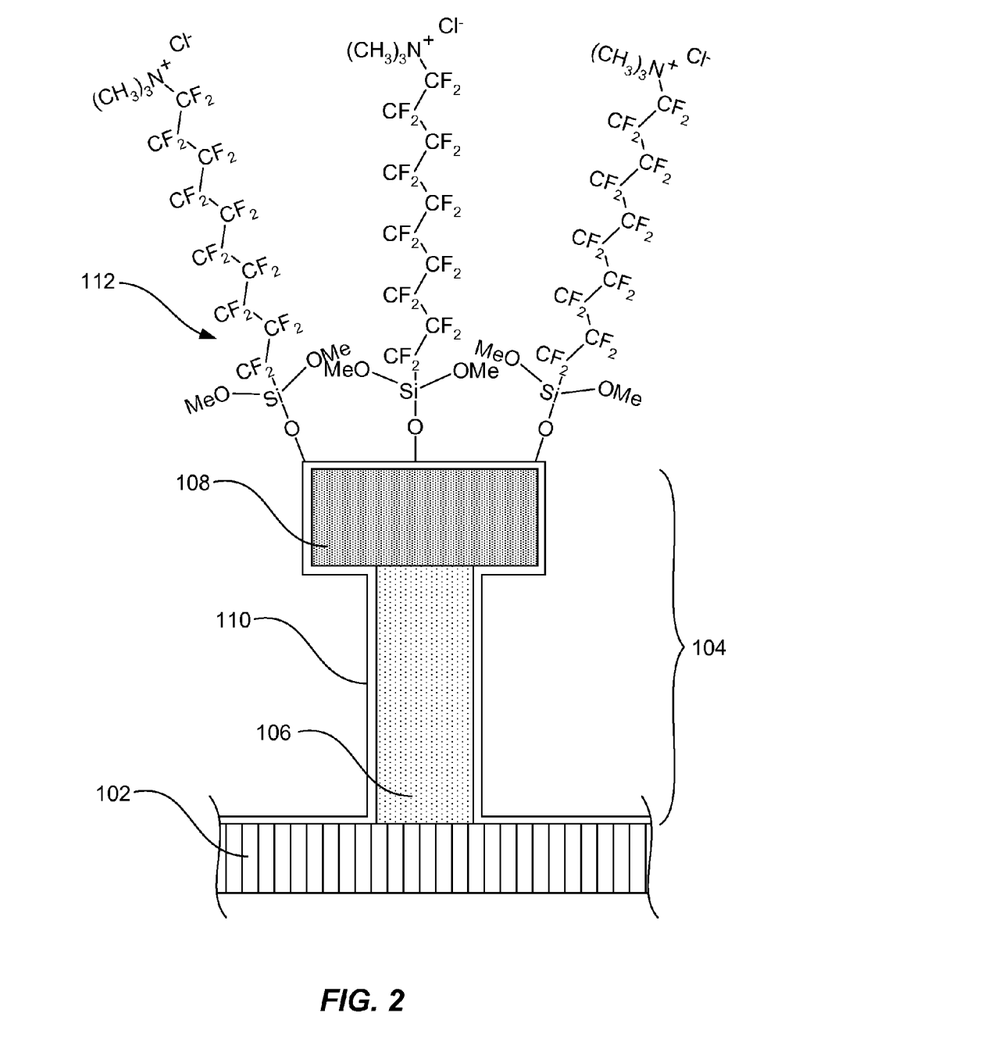
FIG. 2 is a cross-sectional view of a chemical sensing device in accordance with another example of the present disclosure.

Referring to FIG. 2, an expanded view of a single elongated nanostructure having functional groups bonded thereto is illustrated. It is noted that the elements of FIG. 2 are not necessarily drawn to scale, nor does it represent every chemical sensing device available for use herein, i.e. it provides merely an exemplary embodiment of one chemical sensing device having one specific set of functional groups. In this example, the chemical sensing device 200 can include a substrate 102 having an elongated nanostructure 104 attached thereto. The elongated nanostructure can include a columnar structure 106 with a metallic cap 108 deposited thereon. The elongated structure and substrate can further include a metal oxide coating 110 coated thereon. Quaternary amine functional groups 112 are attached to the metallic oxide via a perfluoroalkyl linkage with trimethoxysilyl attachment groups.

Figure 3:
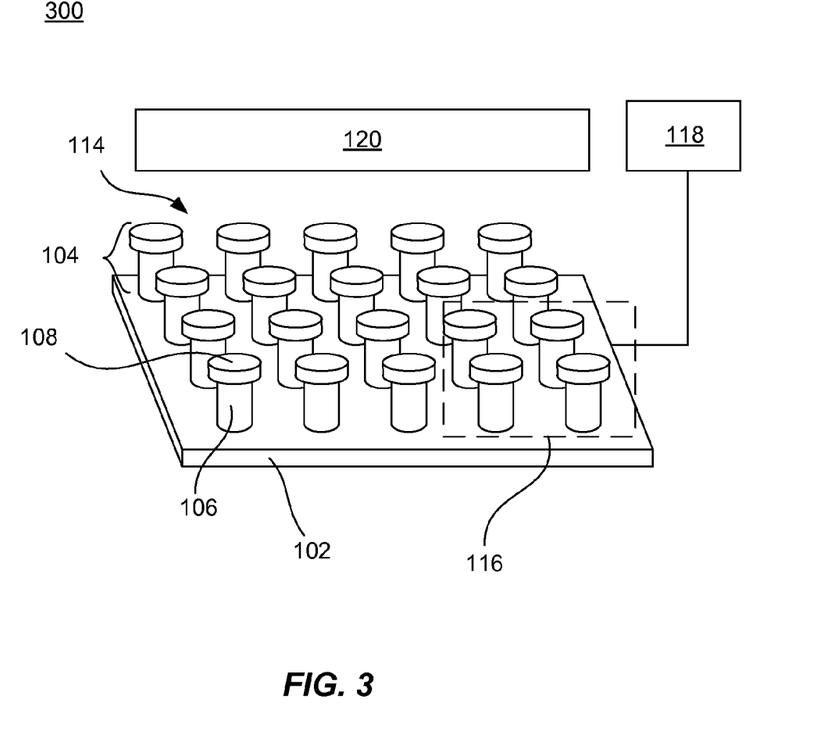
FIG. 3 is a perspective view of a chemical sensing device in accordance with an example of the present disclosure.

Referring to FIG. 3, a chemical sensing device 300 can include a substrate 102 having an elongated nanostructures 104 attached thereto. The elongated nanostructures can include columnar structures 106 with a metallic caps 108 deposited thereon. The device can further include a metal oxide layer (not shown) coating the elongated nanostructures and substrate. The metallic caps can have functional groups (not shown) attached thereto. The plurality of nanostructures can form an array 114 with a sub-array 116. The chemical sensing device can further include a detector 118 operatively coupled to the nanostructures. Additionally, a source of excitation energy 120, such as a light source or a laser source, is also shown.

In use, these devices can have a variety of functions, as would be recognized by one skilled in the art, and one particular use is provided herein by way of example. To illustrate, a target molecule can be exposed to a chemical sensing device such as one of the devices described herein, trapping the target molecule within the chemical sensing device to generate a trapped target molecule. Excitation energy can then be applied to the trapped target molecule and emitted energy from the trapped target molecule can be measured. In one example, the excitation energy and the emitted energy can be electromagnetic energy. Additionally, additional techniques can include flushing the trapped metal target molecule from the chemical sensing device. As such, the present devices can be reusable and/or can be recyclable.

Figure 4:
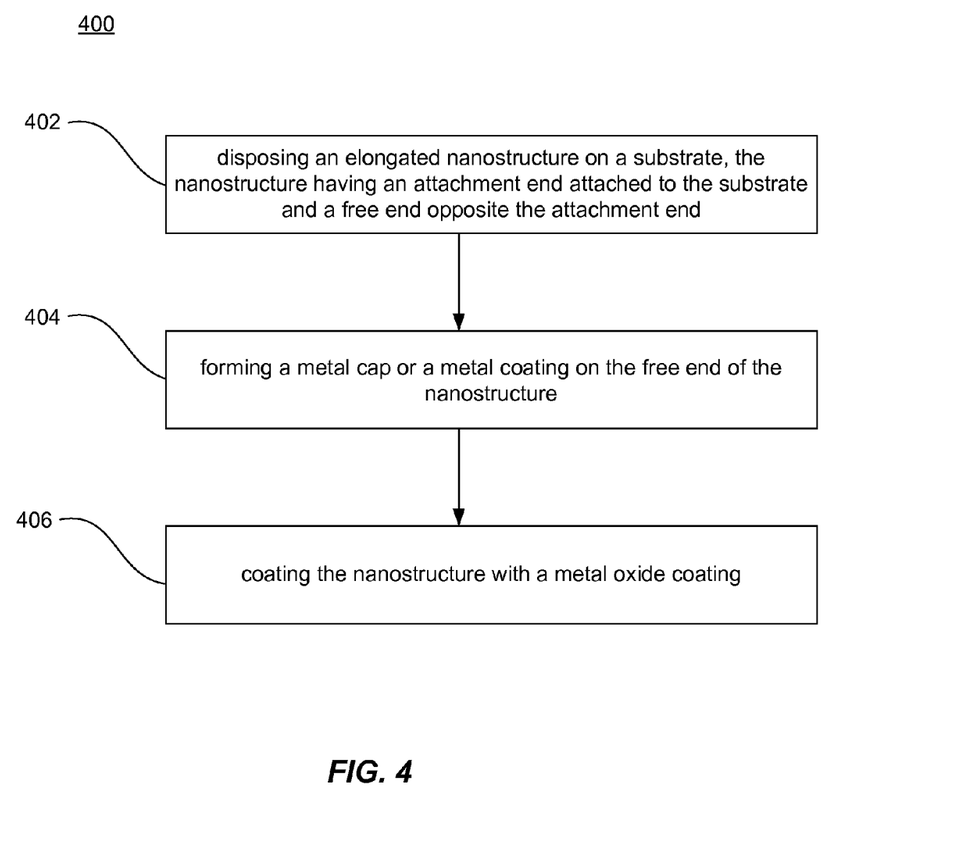
FIG. 4 is a flow chart of a method in accordance with an example of the present disclosure.

Referring to FIG. 4, a method of stabilizing a nanostructure 400 can include disposing 402 an elongated nanostructure on a substrate, the nanostructure having an attachment end attached to the substrate and a free end opposite the attachment end, forming 404 a metal cap or a metal coating on the free end of the nanostructure; and coating 406 the nanostructure with a metal oxide coating.

Figure 5:
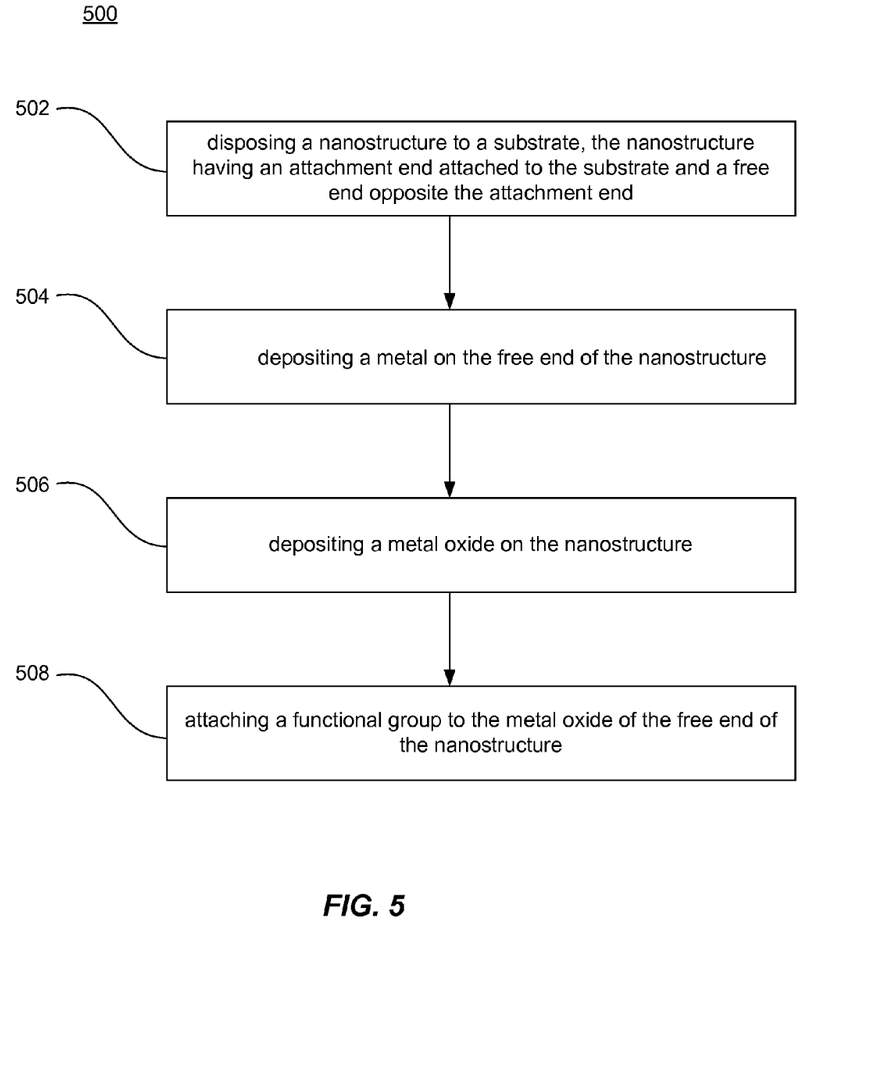
FIG. 5 is a flow chart of a method in accordance with an example of the present disclosure.

Referring to FIG. 5, a method of making a chemical sensing device 500 can include disposing 502 a nanostructure to a substrate, the nanostructure having an attachment end attached to the substrate and a free end opposite the attachment end; and depositing 504 a metal on the free end of the nanostructure; depositing 506 a metal oxide on the nanostructure. In one specific example, an additional step of attaching 508 a functional group to the metal oxide of the free end of the nanostructure can be carried out as well, if the desire is to include a functional group on the metal oxide coating.

It is noted that, as used in this specification and the appended claims, the singular forms "a," "an," and "the" include plural referents unless the context clearly dictates otherwise.

As used herein, a plurality of items, structural elements, compositional elements, and/or materials may be presented in a common list for convenience. However, these lists are to be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

EXAMPLES

The following examples illustrate embodiments of the disclosure that are presently known. Thus, these examples are not to be considered as limitations of the disclosure, but are merely in place to teach how to make devices of the present disclosure. As such, a representative number of devices and their method of manufacture are disclosed herein.

Example 1

Preparation of Nanostructure with Basic Functional Group

Scheme 1 describes an example of a positively charged elongated nanostructure 2 obtained by reaction of metal oxide coated nanostructure 1 with reactive fluorinated silane reagent with quaternary ammonium salts.

The acronym MOCN represents a metal oxide coated nanostructure; $R_1$, $R_2$ and $R_3$ can be independently hydrogen or any alkyl or branched alkyl groups, which include, but is not limited to methyl, ethyl, propyl, isopropyl, butyl, isobutyl, n-octyl, n-decyl, n-dodecyl, n-tetradecyl, etc.; X represents any functional groups that can react with hydroxyl groups, such as $Cl^-$, MeO, EtO, PrO, etc.; n represents the integer form 1 to 15; Y represents negative charged groups, such as halogen anion, carboxylic acid anion, phosphoric acid anion, sulfuric acid anion, hexafluorophosphurs anion, tetraphenyl boronic anion, etc.

Example 2

Preparation of Nanostructure with Perfluoroalkyl Group

Scheme 2 describes an example of perfluoroalkyl group surface treatment on nanostructure surface. A coupling reaction of metal oxide coated nanostructure 1 with reactive perfluorinated silane reagent gave perfluoroalkyl groups attached to the nanostructure to form nanostructures 3, which is hydrophobic.

The acronym MOCN represents a metal oxide coated nanostructure and n represents the integer from 1 to 15.

Scheme 3 lists a series of potential reactive fluorinated materials that can react with the hydroxyl groups on the pigment surfaces to introduce fluorinated materials including small molecules, oligomers and polymers. They contain reactive functional groups as set forth below in Scheme 3, such as acid chloride 5, active ester 6, isothiocyanate 7, trimethoxysilanes 8 and 9. For the trimethoxysilanes 8 and 9, n can range from 1 to 15, x and y can range from 1 to 10000, $Rf_1$-$Rf_5$ can be perfluoroalkyl groups containing 1 to 10 carbons. These reactive functional groups can all react with hydroxyl groups to form covalent bonded fluorinated material treated surfaces.

Scheme 3

While the disclosure has been described with reference to certain examples, those skilled in the art will appreciate that various modifications, changes, omissions, and substitutions can be made without departing from the spirit of the disclosure. It is intended, therefore, that the disclosure be limited only by the scope of the following claims.

What is claimed is:

1. A chemical sensing device, comprising: a substrate; an elongated nanostructure having an attachment end and a free end opposite the attachment end, the attachment end affixed to the substrate and the free end comprising a metal, wherein the metal comprises at least one of a metal coating and a metal cap at the free end; and a metal oxide coating applied to the elongated nanostructure.

2. The chemical sensing device of claim 1, further comprising a functional group attached to the metal oxide coating via covalent bond.

3. The chemical sensing device of claim 2, wherein the functional group comprises an attachment functional group (A), a spacer group (B), and a target functional group (FG) according to formula I:

A-B-FG (I)

wherein A is an organic functional group bound to the nanostructure, B is substituted or unsubstituted, linear or branched alkyl or aryl, and FG is an organic functional group capable of adsorbing a target molecule.

4. The chemical sensing device of claim 2, wherein the functional group is formulated to selectively bind a metal ion, an organic compound, or a hydrogen ion.

5. The chemical sensing device of claim 1, wherein the metal oxide is selected from the group of silicon oxide, titanium oxide, zinc oxide, aluminum oxide, gallium oxide, indium oxide, zirconium oxide, hafnium oxide, tantalum oxide, and mixtures thereof.

6. The chemical sensing device of claim 1, wherein the metal is selected from the group of gold, silver, copper, aluminum, platinum, and mixtures thereof.

7. The chemical sensing device of claim 6, wherein the chemical sensing device is sensitive enough to detect the metal ion, the organic compound, or the hydrogen ion at a concentration of 1 ppt.

8. The chemical sensing device of claim 1, further comprising a detector operatively coupled to the coated nanostructure, wherein the detector is selected from the group of a colorimeter, a reflectometer, a spectrometer, a spectrophotometer, a Raman spectrometer, an optical microscope, and an instrument for measuring luminescence.

9. The chemical sensing device of claim 1, further comprising a plurality of the elongated nanostructures forming an array.

10. The chemical sensing device of claim 9, wherein the array includes sub-arrays, the sub-arrays having individual selectivity for a target molecule, the target molecule individually selected from the group of a metal ion, an organic compound, and a hydrogen ion.

11. A method of stabilizing a nanostructure, comprising: disposing an elongated nanostructure on a substrate, the nanostructure having an attachment end attached to the substrate and a free end opposite the attachment end; forming a metal cap or a metal coating on the free end of the nanostructure; and coating the nanostructure with a metal oxide coating.

12. The method of claim 11, wherein the metal oxide coating is selected from the group of silicon oxide, titanium oxide, zinc oxide, aluminum oxide, gallium oxide, indium oxide, zirconium oxide, hafnium oxide, tantalum oxide, and mixtures thereof.

13. A method of making a chemical sensing device, comprising: disposing a nanostructure to a substrate, the nanostructure having an attachment end attached to the substrate and a free end opposite the attachment end; depositing a metal on the free end of the nanostructure; and depositing a metal oxide on the nanostructure.

14. The method of claim 13, further comprising the step of attaching a functional group to the metal oxide of the free end of the nanostructure.

15. The chemical sensing device of claim 1, wherein the chemical sensing device comprises a chemical sensing device to analyze a chemical using Surface Enhanced Raman Spectroscopy.

16. The method of claim 11, further comprising attaching a functional group to the metal oxide coating via a covalent bond.

17. The method of claim 16, wherein the functional group comprises an attachment functional group (A), a spacer group (B), and a target functional group (FG) according to formula I:

$$A\text{-}B\text{-}FG \quad (I)$$

wherein A is an organic functional group bound to the nanostructure, B is substituted or unsubstituted, linear or branched alkyl or aryl, and FG is an organic functional group capable of adsorbing a target molecule.

18. The method of claim 13, wherein depositing the metal oxide comprises depositing using at least one of automatic layer deposition and E-beam sputtering.

19. The method of claim 13, wherein depositing the metal oxide coating comprises depositing a metal oxide coating selected from the group of silicon oxide, titanium oxide, zinc oxide, aluminum oxide, gallium oxide, indium oxide, zirconium oxide, hafnium oxide, tantalum oxide, and mixtures thereof.

20. The method of claim 15, wherein the functional group comprises an attachment functional group (A), a spacer group (B), and a target functional group (FG) according to formula I:

$$A\text{-}B\text{-}FG \quad (I)$$

wherein A is an organic functional group bound to the nanostructure, B is substituted or unsubstituted, linear or branched alkyl or aryl, and FG is an organic functional group capable of adsorbing a target molecule.

* * * * *